United States Patent [19]
Shofner et al.

[11] Patent Number: 5,394,480
[45] Date of Patent: Feb. 28, 1995

[54] TOPOLOGICAL MAP MAKER

[75] Inventors: Frederick M. Shofner; Joseph C. Baldwin; Benjamin M. Kacenas; Youe-T. Chu, all of Knoxville, Tenn.

[73] Assignee: Zellweger Uster, Inc., Knoxville, Tenn.

[21] Appl. No.: 762,613

[22] Filed: Sep. 19, 1991

[51] Int. Cl.$^6$ .............................................. G06K 9/00
[52] U.S. Cl. ................................. 382/1; 73/863.23; 250/559; 348/88; 382/8
[58] Field of Search ................. 358/101, 107; 382/1, 382/8; 73/863.23; 131/346; 348/88, 92; 250/559; 377/10

[56] References Cited

U.S. PATENT DOCUMENTS

| | | | |
|---|---|---|---|
| 4,561,018 | 12/1985 | Berthel et al. | 358/107 |
| 5,012,681 | 5/1991 | Lentzen | 73/863.23 |
| 5,020,111 | 5/1991 | Weber | 382/42 |
| 5,044,380 | 9/1991 | Crooks et al. | 131/329 |
| 5,073,857 | 1/1992 | Peters et al. | 358/107 |

FOREIGN PATENT DOCUMENTS

| | | | |
|---|---|---|---|
| 1377453 | 12/1974 | Australia | G01N 9/00 |
| 484029 | of 0000 | Belgium | G01N 33/36 |
| 422616A2 | 4/1991 | European Pat. Off. | G01N 15/14 |
| 3928279 | 2/1991 | Germany | G01N 33/36 |
| 462424 | 3/1937 | United Kingdom | G01N 33/36 |
| 9114169 | 9/1991 | WIPO | G01N 15/14 |

*Primary Examiner*—Leo H. Boudreau
*Attorney, Agent, or Firm*—Luedeka, Neely & Graham

[57] ABSTRACT

A map maker is disclosed in which a physical map is produced by depositing fluid entrained entities, such as cotton fibers, trash and neps, in a pattern on a surface, such as a nylon mesh surface. Each position in the pattern is uniquely associated with data produced by another monitor to provide topological mapping between the data event map and the physical map. In one embodiment, a drive system and computer are used to control the position of a surface relative to a nozzle that deposits the entities on the surface and relative to a camera that scans the map formed on the surface. In the preferred embodiment, the map is planar, but an alternate cylindrical map is shown. Also, an embodiment is shown in which a map maker is incorporated into a carding machine.

15 Claims, 5 Drawing Sheets

TOPOLOGICAL MAP MAKER

FIELD OF INVENTION

The present invention relates to mapping entities and, particularly, relates to apparatus which produces a physical mapping function wherein entities are deposited in a pattern on a filter media for examination.

BACKGROUND AND SUMMARY OF INVENTION

A wide variety of substances are or may be entrained in fluid, such as air, for study including, for example, cotton fibers, polyester fibers, other textile fibers, coffee, other particulate foodstuffs, etc. Such entrained material nearly always contains foreign matter, such as trash in cotton, and interesting variations in the material itself may be present. In cotton, tangled balls of fibers called neps, as well as trash, are interesting because both affect the utility and value of the cotton. In polyester fiber, foreign and undesirable entities known as shot or fused fibers, as well as neps, are interesting because these entities also degrade the performance of the raw material.

One device that measures such air entrained entities including neps is sold under the trade name AFIS by Zellweger Uster, Inc. In this device, a sample of entities, such as cotton fiber containing neps and trash, are fed to the machine, individualized, entrained in an airstream, and optically measured. While such devices work well to measure such things as neps in a cotton sample, it would be desirable to have fast and economical methods or devices to supplement, verify and/or calibrate the data produced by the AFIS device. In this application, it is highly desirable to establish a time relationship with the AFIS data event and the location of the entity on the physical nep. Another area of application is to directly monitor such foreign matter entities, without a separate optical measure. A final area of application is to monitor the main component of the sample itself, such as individual fibers.

More generally, the objectives of this invention are to topologically map the locations of entities in space and/or time, to map their locations in space with data events in time, or to map between different data events.

Topology, among other things, deals with mathematical relationships between points on general surfaces. In this invention we are concerned with entities such as neps or trash particles or fibers which comprise volumetric fiber samples within which it is impractical or impossible to "see" or examine them without interference; that is, it is impractical or impossible to measure them. We are concerned with presentation; this means transforming or mapping volumetrically-located entities onto surfaces or into lines where they can be measured substantially individually and thus without interference. The transformation leaves the entity properties substantially unchanged, or invariant.

Thus a first application of topological mapping is presentation of a volumetric sample of entities onto surfaces or onto lines wherein their presentation enhances or enables measurement. This mapping is described by the general transform operation $$\bar{S}_v \rightleftharpoons \bar{S}_s \quad (1)$$

where $\bar{S}_v$ describes each entities' location in the volumetric sample and $\bar{S}_s$ describes its location when presented for measurement on a surface. This surface is called PHYSICAL MAP of the entities. The locations can be time-dependent.

Further to this objective of topological mapping, we establish the functional relationship of surface-located entities to measurement data events $\bar{E}(t)$ $$\bar{S}_s(t) \rightleftharpoons \bar{E}(t)$$

where $\bar{E}(t)$ is an n-dimensional vector, $$\bar{E}(t) = [V_1(t), V_2(t), \ldots V_n(t)], \quad (2)$$

where the elements $V_1(t)$ are physical responses such as voltage, force, time, etc.

The terminology "event" relates, for example, to a voltage waveform in time. Time need not be explicit, however, in Equation 2. The measurement data for the entities is called a DATA MAP.

It can be now appreciated that examination of the physical map of entities in concert with the data map is most useful. One may investigate relationships between events and entities or between events in two or more data maps or even between entities on two or more physical maps.

The physical and data maps can, for simplistic convenience, be planar or to the same scale. Both serve archival purposes. Modern computational methods and apparatus enable high-powered analytical investigations of relationships between mapped entities and events. In providing for apparatus and methods to meet the topological mapping objectives of this invention, a powerful new analytical tool is enabled.

There follow clarifying comments. Let the mappings be (1) the ordered individualization of entities such as fibers, neps and trash in bulk fiber samples, one at a time, followed by (2) measurement of these individual entities, followed next by the (3) presentation of all sample entities in serpentine tracks on planar mesh and (4) concluded by measurement of the entities when so preferably presented for examination.

A unique spatial relationship is provided between the location of the entities in the original volume and their position in the tracks (or along a line). A unique relationship is provided between the locations $\bar{S}_s(t)$ of the spheres and entities on the physical map and their data events $\bar{E}(t)$. These mapping relationships are useful in themselves but we have special interest in relating the temporal measurement events $\bar{E}_2$ in Step 2 with those in Step 4, $\bar{E}_4$. We are topologically relating two data maps to investigate the data relationships for each entity removed from the volume sample (Step 1) and presented in the preferred planar pattern (Step 3).

To further simplify, assume that Step 4 is a reference method such as optical microscopy. We seek to relate these data to the event data of Step 2. This will be appreciated as a calibration procedure.

The data events and maps in either Steps 2 or 4 may be one dimensional, such a peak voltage for each nep, as in an AFIS sensor; two dimensional, such as charge-coupled signals representing images of a trash particle; or three-dimensional such as a holographic record of a pneumatically-transported fiber.

The present invention also provides an efficient apparatus and method for monitoring the properties of fluid entrained entities. Such monitoring may be for independent direct measurements or for correlation with data from other instruments for the purpose of mutually verifying data or calibrating one of the instruments.

In accordance with the present invention, a physical map is produced by depositing fluid entrained entities, such as cotton fibers, trash and neps, in a pattern on a surface, such as a nylon mesh surface. When used with another instrument, preferably each position in the pattern is uniquely associated with data produced by the other monitor so that for a particular set of data one may locate on the physical map the entities that produced the data. This represents a topological mapping between the data event map and the physical map.

To produce the physical map of the preferred embodiment, an appropriate filter is interposed in an airstream containing entities and is moved relative to the airstream in a pattern at a known speed. Thus, the entities are deposited in a pattern on a filter.

In the preferred embodiment, a physical map apparatus is incorporated into an AFIS device. In such combination, an entity sample is fed into a separator that separates and individualizes the various entities in the sample and the individual entities are transported in a conduit by a vacuum driven airstream to an optical measuring station where characteristics of the entities are optically measured and optical data events are produced. From the optical station, the entities are carried by suction through a conduit to the physical map apparatus where a nozzle directs the entities through an appropriate filter. A suction tube, positioned on the opposite side of the filter from the nozzle, draws air from the nozzle and a suction pump is connected to the suction tube for providing the needed suction. As air passes from the nozzle, through the filter and into the suction tube, entities are caught by and deposited on the filter. Hereafter, the terms physical map and filter map are used interchangeably.

A drive mechanism is connected to move the mesh filter relative to the nozzle in a pattern to thereby deposit entities in such pattern on the filter and create a filter map.

A computer is connected to receive and record optical data produced by the optical measuring station as a function of time and it is also connected to record the position of the nozzle relative to the filter as a function of time. In this manner, a time-stamped map is produced on the filter. A correction factor indicative of the time that it takes for the entities to travel from the optical measuring station to the filter is provided to the computer and, using the correction factor, the computer correlates the optical data to positions in the pattern on the filter map. These correlated data are stored and selectively used or displayed.

Sensors are provided for sensing characteristics of the entities on the filter map as a function of map position. In a preferred embodiment, a first camera is positioned adjacent to the nozzle and a second camera is positioned adjacent to the suction tube. Stepping motors and translation tables drive the mesh filter in X, Y directions relative to the nozzle, the suction tube and the two cameras. A control system is provided between the computer and the stepping motors so that the computer precisely controls the position of the mesh filter, and the computer is provided with the position of the nozzle and the cameras. With this information, the computer is programmed to control the stepping motors and cause the filter to move in a reversing raster scan so that parallel rows of entities are deposited on the filter. Also, the computer is programmed to move the rows of entities into view of the cameras as desired. Preferably, the cameras are positioned relative to the nozzle to view two rows behind the nozzle as the entities are being deposited on the filter. Thus, as the entities are being deposited, the cameras are viewing a previously deposited row. In this manner, the process of depositing rows of entities also functions to scan the rows with the cameras. As the cameras scan, a series of video images are stored in the computer and are correlated to the map position that the cameras viewed, and it will be recalled that the stored optical data is also correlated to the map positions. Thus, the optical data, the map positions, and the video images are all cross-correlated and each may be output as a function of the others.

In another embodiment, the filter map is a circular cylinder and a helical pattern is produced.

Of course, the video or other measurements may be made at a later time since the physical map may be retained permanently.

BRIEF DESCRIPTION OF THE DRAWINGS

The present invention may best be understood by reference to a Detailed Description of a preferred embodiment when considered in conjunction with the Drawings in which.

DETAILED DESCRIPTION

Figure 1:
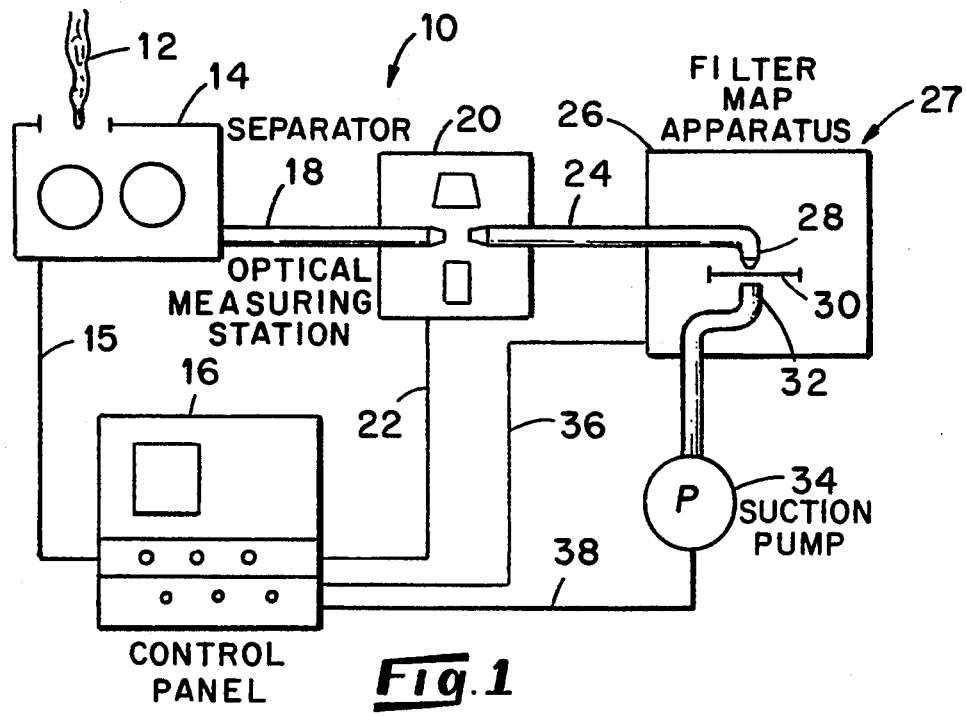
FIG. 1 is a somewhat schematic diagram of the entity monitoring system.

Referring now to the drawings in which like reference characters designate like or corresponding parts throughout the several views, there is shown in FIG. 1 an entity monitoring apparatus 10 in which a sample 12 of entities is fed to a separator 14. For example, the sample 12 may be raw cotton which includes cotton fibers and foreign matter such as neps and trash and the separator 14 functions to individualize the fibers and neps and feed them through a suction conduit 18 to an optical measuring station 20. The separator 14 preferably removes most of the trash before delivering the individual entities to conduit 18 but in other embodiments the separator 14 may be configured to feed separate entities of trash to the conduit 18.

A control panel 16, which includes an IBM AT compatible computer, is connected through control lines 15 to control the operation of the separator 14. Likewise, the control panel 16 is connected via lines 22 to control the measuring station 20 and receive data therefrom. In the preferred embodiment, the separator 14, the control panel 16 and the optical measuring station 20 are all part of a conventional AFIS machine sold by Zellweger Uster, Inc., and the conduit 18 has a one-half inch inside diameter and an airflow of 3.9 cubic feet per minute.

As air and entities pass through the optical measuring station 20, the entities are illuminated by a light source and a variety of optical measurements are taken which may include the amount and duration of forward scattering, back scattering and light extinction. For each entity passing through the optical measuring station 20, a set of optical data is produced. This electro-optical data event, including its time of occurrence, is transmitted to the computer of control panel 16 and stored as a function of time. That is, the computer stores both the optical data and the time at which the data was taken.

After the entities leave the optical measuring station 20, they travel in a suction driven airstream through conduit 24 into a sealed chamber 26 which contains and is a part of the filter map apparatus 27. The entities are expelled by nozzle 28 and directed toward a filter 30 which, when cotton is being studied, is preferably conducted of a 20 denier, circular knit nylon mesh. The filaments have a diameter of about eighteen (18) microns and, when the filter is taut, the filaments are separated by one millimeter in one dimension and in the perpendicular dimension are alternately separated by one (1.0) millimeter, then one quarter (0.25) millimeter. Of course, the media of filter 30 should be adjusted according to the physical characteristics of the entities being studied. The purpose of filter 30 is to provide a surface for the deposit of entities and in some embodiments a solid surface or paper would be an appropriate surface. As used herein, the term "filter" does not necessarily imply that fluid must pass through it. The essential characteristic is that entities be deposited on it.

Positioned below the filter 30 and directly below the nozzle 28 is a suction tube 32 that is connected to a suction pump 34 which provides the vacuum or suction that pulls the entities from the separator 14, through the station 20, through the nozzle 28 and into the mesh filter 30. When a cotton sample is used, typically more than 99% of the fiber weight is captured by the filter 30.

The control panel 16 controls the operation of the filter map apparatus 27 through lines 36 and, also, receives data through lines 36 as will be hereinafter described in greater detail. Likewise, the control panel 16 controls the pump 34 through lines 38.

Figure 2:
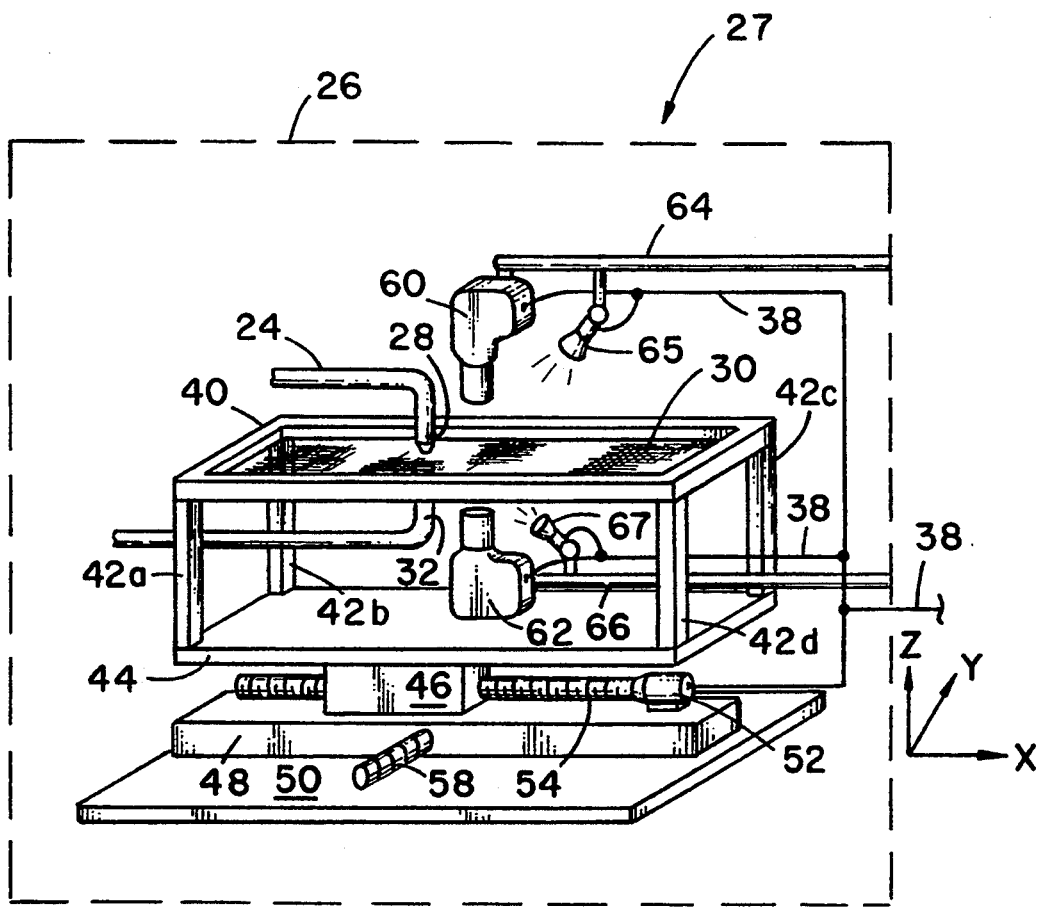
FIG. 2 is a somewhat diagrammatic perspective view of the filter map apparatus.
Figure 3:
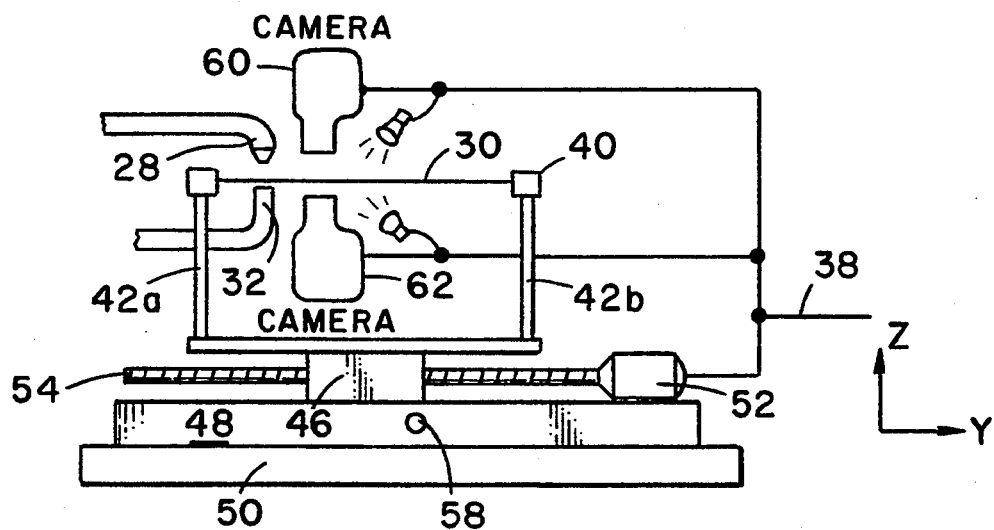
FIG. 3 is a somewhat diagrammatic side view of the entity mapping apparatus.
Figure 4:
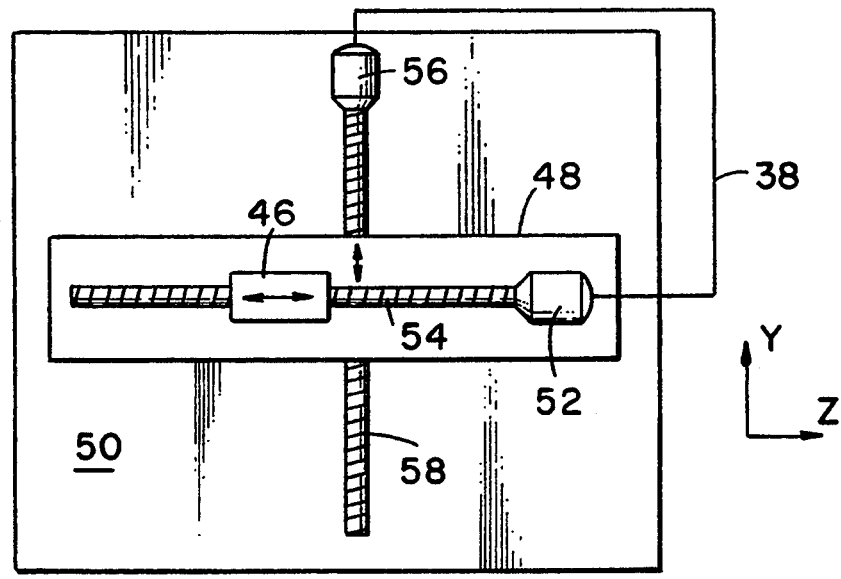
FIG. 4 is a top view of the translation tables that move the filter map.

Referring now to the somewhat diagrammatical FIGS. 2, 3 and 4, the filter map apparatus 27 is shown in greater detail. A nylon mesh 30 is stretched tautly in a frame 40 and legs 42a-d extend downwardly to rest on a platform 44 and thereby support the frame 40 and filter 30 in a raised position above the platform 44. A translation table 46 is fixedly mounted to the underside of platform 44 and is disposed for motion on a drive table 48 which, in turn, is supported for sliding motion on support table 50. A stepper motor 52 and a screw 54 drive the table 46 in the X direction (left and right as shown in FIGS. 2, 3 and 4) under the control of the computer 16 and, likewise, stepper motor 56 and screw 58 drive the table 48 in the Y direction (into and out of the page as shown in FIGS. 2 and 3) in response to commands from the computer 16. Preferably, the tables 46, 48 and 50 are mechanically interconnected by roller bearings to allow free travel therebetween, but simple sliding movements could be used also. Thus, in this construction, the filter 30 is moved relative to the nozzle 28 and suction tube 32 and, as the entities escape the nozzle 28, they are deposited in any desired pattern on the filter 30.

Figure 5:
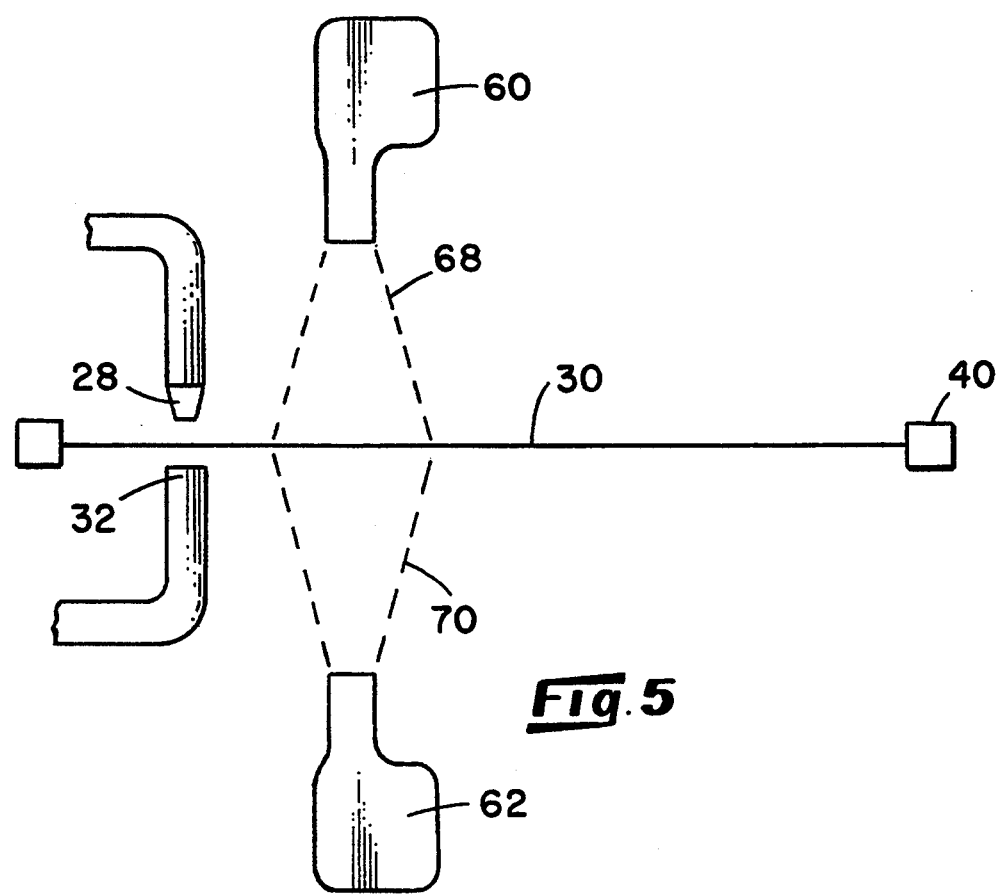
FIG. 5 is a diagrammatic side view showing the nozzle and cameras.

As best shown in FIGS. 2, 3 and 5, a pair of cameras 60 and 62 are held by mounts 64 and 66 in stationary positions relative to the nozzle 24 and the suction tube 32. As indicated by field of view lines 68 and 70 in FIG. 5, camera 60 will view the top side of the filter 30 immediately adjacent to the nozzle 28 and camera 62 will view the lower side of filter 30 immediately adjacent to the suction tube 32. Lights 65 and 67 illuminate the top and bottom surfaces of filter 30 including the field of view of the cameras 60 and 62. The cameras 60 and 62 and lights 65 and 67 may operate in any desired frequency spectrum, visible or non-visible. In some applications, near-infrared cameras and lights are desirable for examining characteristics of fibers such as sugar content, moisture content, type of foreign matter content, etc.

Figure 6:
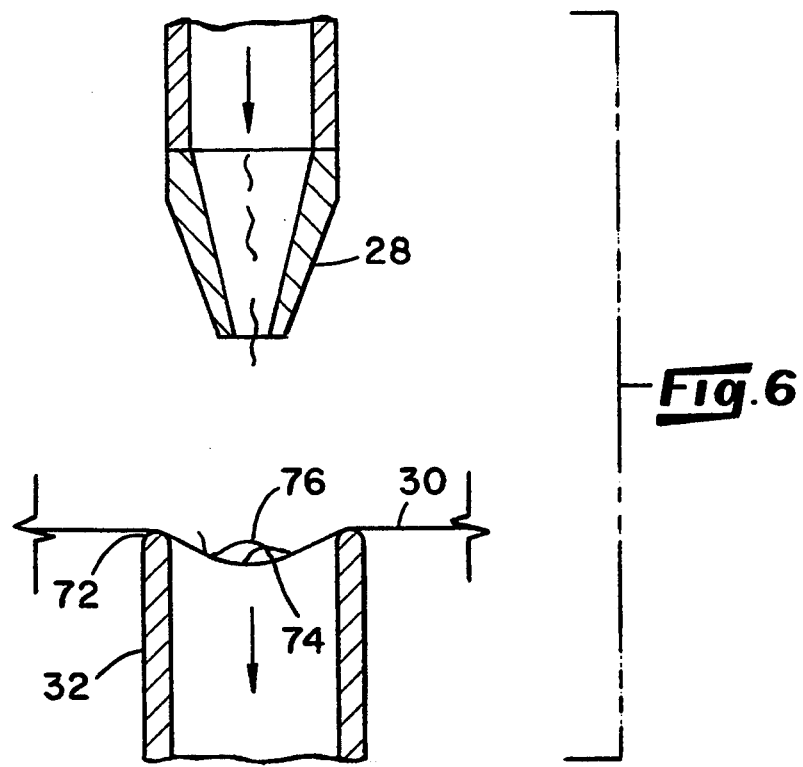
FIG. 6 is a cross-sectional view showing the nozzle and suction tube.

Referring now to FIG. 6, a cross-sectional view of the nozzle 28, the suction tube 32 and the filter 30 is shown. In the preferred embodiment, the nozzle 28 exit has a diameter of 4.85 mm. and the nozzle inlet has a diameter of 12.6 mm. with a nozzle length of 90 mm. The suction pipe 32 has a preferred diameter of 12.7 mm. and has a rounded mouth 72. The preferred distance between the nozzle 28 and the top of the tube 32 is approximately 16 mm. and, when the suction is off, the filter 30 is disposed approximately 5 mm. above the mouth 72 of tube 32. However, when the vacuum pump 34 is on, the mesh filter 30 is drawn against and down into the mouth 72 of tube 32 and forms a concave shape 74 inside the mouth 72. This shape facilitates the concentration and deposit of the entities 76 in an accurate position on the mesh filter 30. As the mesh filter 30 moves with respect to the suction tube 32, different portions of the filter 30 are drawn into suction tube 32 and then released from the mouth 72. It will be appreciated that the mesh filter 30 stretches when it is within the mouth 72 of tube 32, thereby increasing the size of the openings in the mesh. When the mesh moves out of the mouth 72, it returns to its original opening size and creates a pinching action on the captured entities 76.

Figure 7:
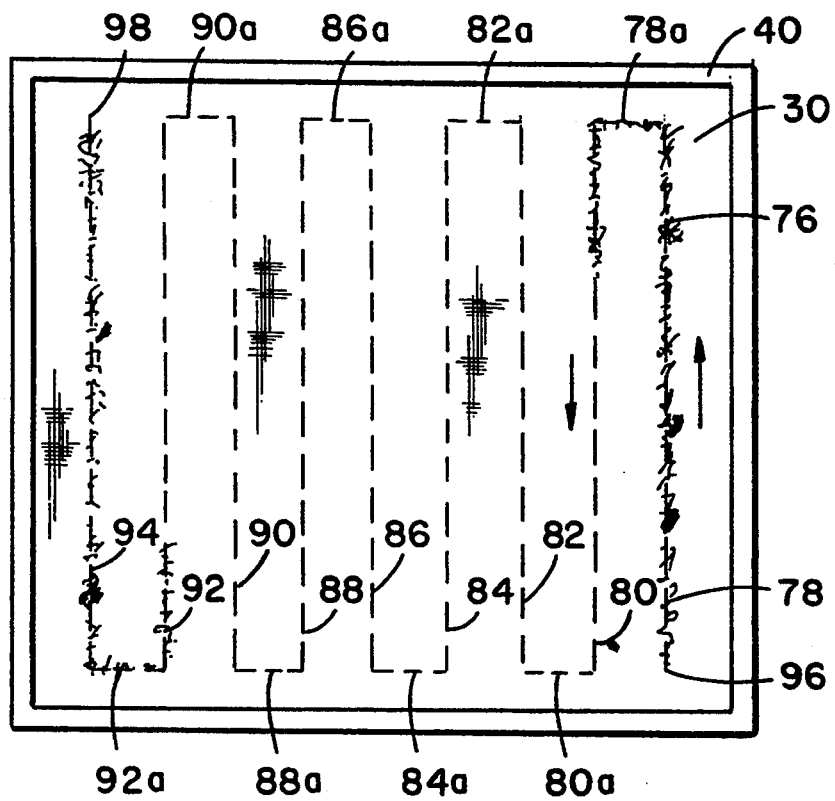
FIG. 7 is a somewhat diagrammatic top view of a planar filter map.
Figure 8:
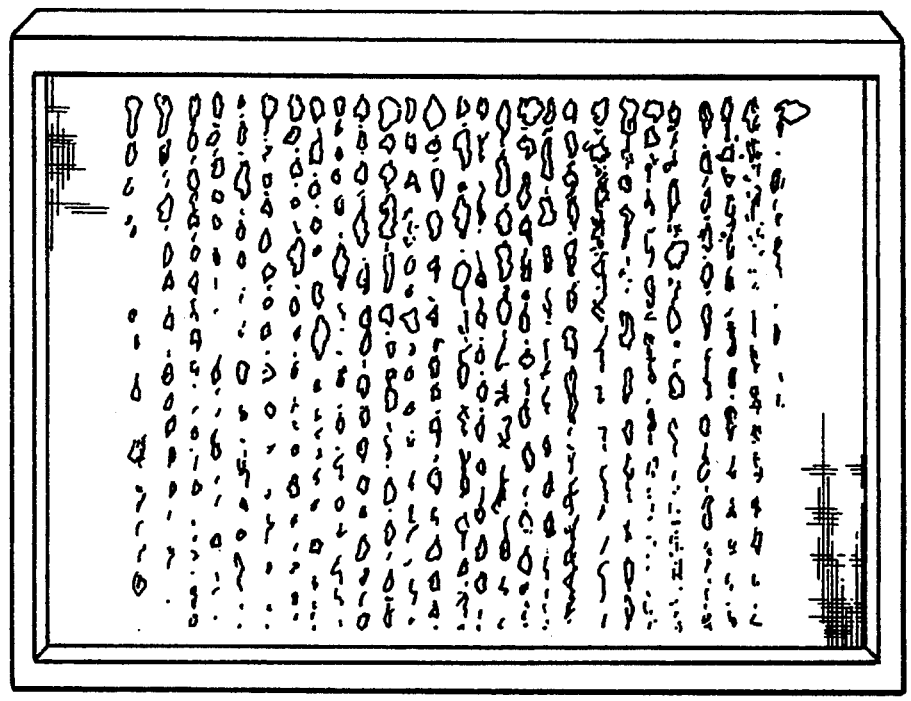
FIG. 8 is a pictorial representation of a map.

Referring now to FIG. 7, a preferred pattern of entities 76 on the filter 30 is shown. A pictorial representation of a typical filter 30 and map is shown in FIG. 8 for greater clarity of illustration. Preferably, the filter 30 is moved by the stepper motors 52 and 56 under the control of control panel 16 to deposit the individual entities 76 in a direction reversing raster or serpentine pattern of rows 78–94 with the first being row 78 and the last being row 94. Any number of rows may be used. As the map 30 moves to deposit entities 76, the computer is recording a "map position" on the filter 30. This map position could be a set of X, Y coordinates, but is preferably a single number indicating a linear position along the continuous rows 78–94. For example, the distance from the beginning 96 of row 78 to the end 98 of row 94 is divided into 1,000 segments and each segment is accorded a map position. The first segment adjacent the beginning 96 is map position 1. The last segment adjacent the end 98 is designated as map position 1,000. Thus, each of the 1,000 segments in the rows 78–94 and the connectors 78a–92a is uniquely identified by a single map position number.

As the entities 76 are deposited on the map 30 in the pattern shown in FIG. 7, a map number is stored in the computer of control panel 16 as a function of time. The storing of a map position in association with a particular time may be referred to as "time stamping" the entity positions. It will be recalled that the optical data produced by the measuring station 20 were also recorded as a function of time and, thus, a map position can be correlated against the optical data, except for the fact that some time is required for the fiber to travel from the measuring station 20 to the filter 30.

In the preferred embodiment, 60 milliseconds are required for the fiber to travel from station 20 to filter 30 and, thus, 60 milliseconds are added to the time stored for each set of optical data. Using this 60 millisecond correction factor, the optical data are then directly correlated to map positions 1 through 1,000 by matching their associated times.

Referring to FIGS. 5 and 7, it will be appreciated that the cameras 60 and 62 are positioned relative to the nozzle so that the cameras 60 and 62 will view the row entities two rows behind the row that is currently being deposited. For example, when rows 78 and 80 are being deposited, the cameras will view nothing. When row 82 is being deposited, the cameras 60 and 62 will be scanning row 78. Likewise, when row 84 is being deposited, the cameras will view row 80. Thus, as the entities 76 are being deposited on the map, they are also being scanned by the cameras 60 and 62. When the last row (row 94) is deposited, an extra two scans are made with the cameras 60 and 62 viewing rows 92 and 94.

In an alternative embodiment, an entirely separate scan can be conducted after all of the rows have been deposited with the filter 30 being moved under the control of panel 16 so that the cameras 60 and 62 retrace the path of the nozzle 28 on the filter 30.

Regardless of how the cameras are caused to scan the filter 30, a sequence of images are produced, associated with a map position and stored in the computer in digital form. For example, when the cameras 60 and 62 are viewing map position 1, images 1a and 1b are stored in association with map position 1. When the cameras 60 and 62 are viewing map position 2, images 2a and 2b are stored in association with map position 2, and so on. Since the optical data have already been correlated with map positions, the images may be correlated with the optical data previously stored in the computer. Thus, for a particular image, the corresponding optical data may be recalled or, for a particular set of optical data, the image of a map position may be recalled. Having the data in this form is useful for verifying and/or calibrating the optical measurements against the images of map locations. For example, it is known that neps in cotton samples produce identifiable optical data characteristics and, thus, the optical data is computer analyzed by conventional techniques used in the AFIS machine to find data indicating the presence of neps. Once a nep is identified using the optical data, the corresponding image of a map position on the filter 30 may be recalled and displayed to an operator who can visually examine each nep that was deposited at the corresponding map location on the filter 30. Alternatively, the image at this map location may be analyzed by the computer to verify that its size and shape is indicative of a nep. In this fashion, the optical data are checked using the stored images of map positions.

It will also be recognized that the map shown in FIG. 7 is, in a sense, recorded visual data. Instead of using the recorded images of map positions, the map itself may be used to check the accuracy of the optical data. For example, when computer analysis finds a particular set of optical data indicating the presence of a nep, the corresponding map position is determined, and the filter 30 is moved to place that map position within the view of cameras 60 and 62. Then, either a computer or an operator views and analyzes the images from the cameras to verify the presence of a nep. Also, once the desired map position is located, any desired measurement may be made on the entities of interest by a wide variety of instruments.

Figure 9:
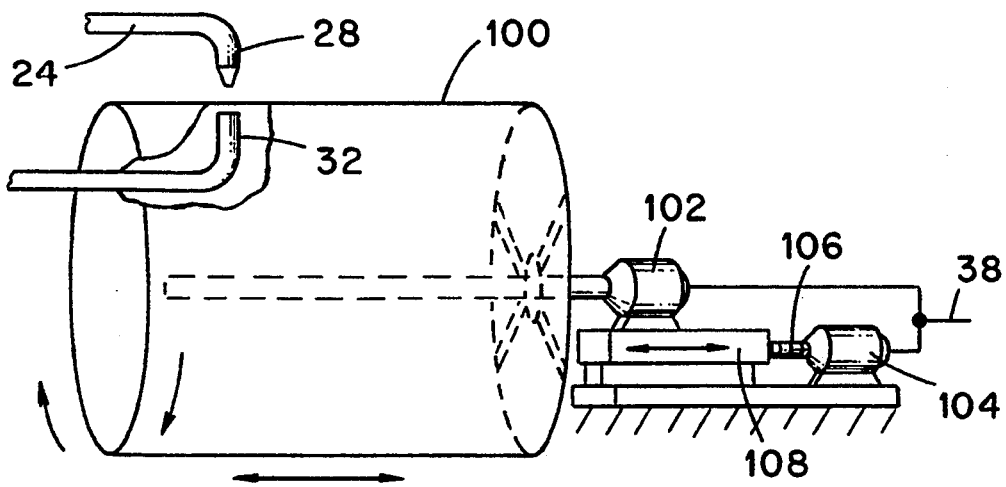
FIG. 9 is a diagrammatical view of a cylindrical map maker.

From the above discussion, it will be appreciated that the present invention provides both a new method for presenting entities for measurement or analysis, for monitoring and storing information derived from characteristics of entities and a method for accurately checking the measurements of other measuring devices. While the invention has been described in connection with a preferred embodiment, it will be understood that the scope of the invention is not limited to this embodiment, but is defined by the appended claims. For example, referring to FIG. 9, it will be appreciated that a cylindrical filter 100 represents a variation of filter 30. In the embodiment of FIG. 9, filter 100 is mounted for rotation on its axis by motor 102 and motor 104 drives screw 106 to move slide bar 108 and filter 100 in a direction parallel to the axis of cylindrical filter 100. In this manner, filter 100 is moved so that nozzle 28 deposits a helical pattern or map of entities on filter 100 that is time-stamped in the manner previously described with regard to filter 30.

Figure 10:
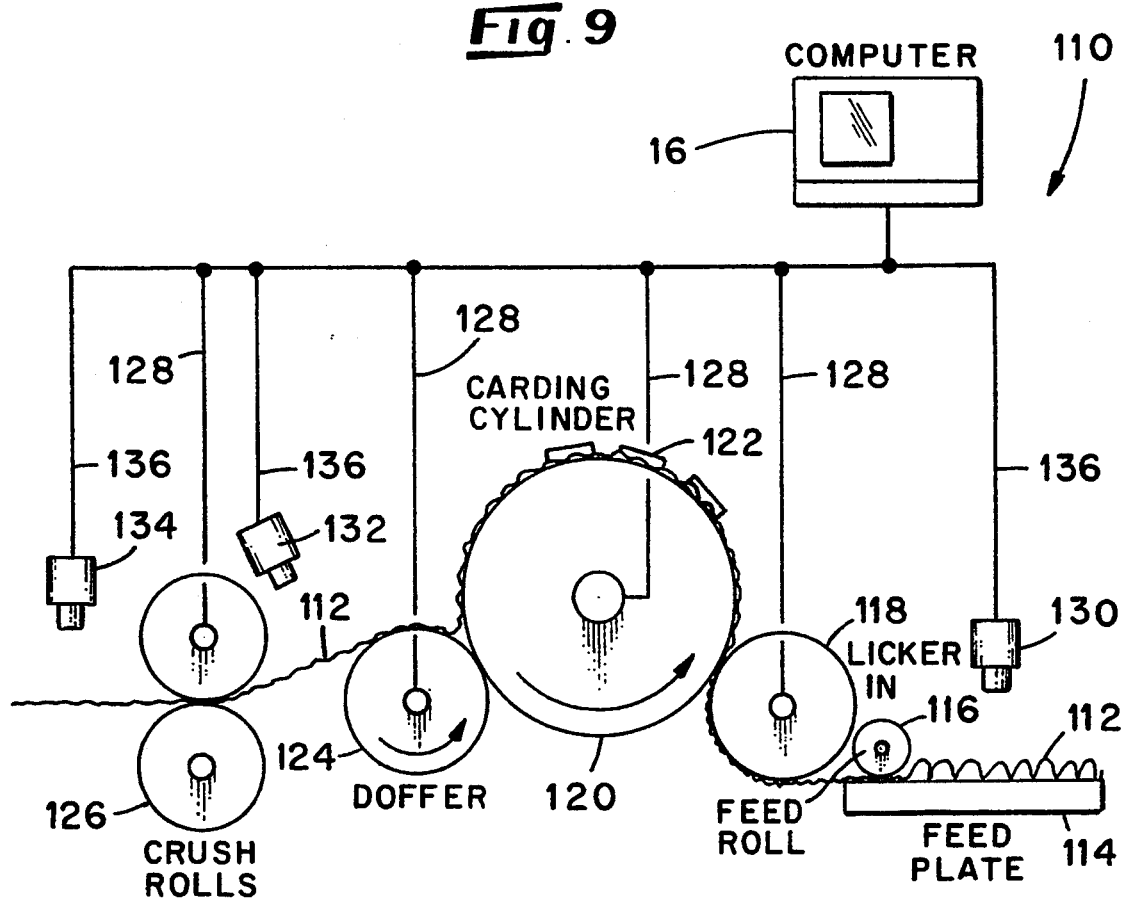
FIG. 10 is a diagrammatical view of a carding machine with a map maker incorporated into it.

Another alternate embodiment is shown in FIG. 10 to illustrate how the map maker may be advantageously incorporated into existing machinery and with appropriate modification, may take advantage of naturally occurring phenomenon. The apparatus 110 of FIG. 10 is a modified carding machine in which a layer of cotton is supplied by a feed plate 114 and feed roll 116 to a licker-in 118 which, in turn, supplies the cotton to a carding cylinder 120. Carding flats 122 work in conjunction with the cylinder 120 and doffer 124 to card the cotton 112 into a thin layer or sheet that is supplied to crusher rolls 126. This mechanical apparatus is mechanically conventional and is typical of many cotton mills.

The computer 116 is connected to receive feedback from and control the drive mechanisms of the licker-in 118, the carding cylinder 120, the doffer 124 and the crush rolls 126 as illustrated by control and feedback lines 128 that are connected between these elements and the computer 116. Sensors are provided to monitor the cotton 112 on the feed table 114, between the doffer 124 and the crush rolls 126, and after the crush rolls 126. For example, the sensors are preferably video cameras 130, 132 and 134. The video cameras are connected by lines 136 to the computer 116 which includes appropriate A to D converters for converting the analog video signals to a digital format and stores the digital video information. As computer 116 stores the video information, the data is time stamped. That is, each of the images from the video cameras 130, 132 and 134 is stored in the computer in association or relation with the time at which the video image was produced. The mechanical speed of the apparatus 110 is constantly monitored by the computer 116 and a time is calculated for cotton to move from the viewing area of camera 130 to the viewing area of camera 132 and, then, to the viewing area of camera 134. Once this delay time or travel time of the cotton is calculated, the digital images from the three cameras may be correlated by using the time-stamp information in the manner previously described with respect to other embodiments. Once the data from the three cameras is correlated, the computer is programmed to recall, display and analyze recorded images as desired.

While FIGS. 9 and 10 represent alternate embodiments of the invention, and it will be understood that the invention is subject to numerous other variations or substitutions of parts without departing from the scope of the invention.

We claim:

1. An apparatus for moving and presenting physical textile entities for measurement or viewing in connection with a previously quantized correlation parameter for mapping the locations of the entities comprising:
   a media having a surface, and
   a map of the physical textile entities deposited on the surface in a pattern that is a function of the correlation parameter, said map including a plurality of discrete map positions, each of said map positions being uniquely associated with the parameter.

2. The apparatus of claim 1 wherein said parameter is time whereby each map position is uniquely associated with the time at which the physical textile entities were deposited on said media surface.

3. The apparatus of claim 1 wherein the parameter comprises a plurality of sets of data and wherein each map position is uniquely associated with one set of data.

4. An apparatus for mapping physical entities comprising:
   a surface adapted to receive a deposit of the physical entities;
   means for producing a stream of the physical entities;
   a sensor disposed in the stream of physical entities for measuring characteristics of the entities and producing an output indicative of the characteristics;
   means for determining a correlation parameter for said physical entities;
   means for presenting the stream of physical entities onto said surface for deposit; and
   means for producing relative movement between said presenting means and said surface to deposit said physical entities on said surface in a pattern corresponding to the movement, said pattern a function of said correlation parameter to produce a map of physical entities on said surface having a plurality of map positions.

5. The apparatus of claim 4 further comprising:
   a computer having a clock for keeping time, being connected to said movement producing means, controlling the relative movement of said presenting means and said surface to produce a map of said physical entities on said surface in a desired pattern having a plurality of discrete map positions, determining the time at which the physical entities are deposited at each map position, and storing the map positions as a function of time of entity deposit.

6. The apparatus of claim 4 further comprising:
   a computer having a clock for keeping time, being connected to said movement producing means, controlling the relative movement of said presenting means and said surface in a desired pattern having a plurality of discrete map positions, determining the time at which the physical entities are deposited at each map position, storing the map positions as a function of time of entity deposit, said computer being connected to said sensor for receiving said sensor output, storing said sensor output as sensor data as a function of time, and correlating the sensor data and the stored map positions by comparing the items stored in association with each of said map positions and said sensor data.

7. The apparatus of claim 4 further comprising at least one camera for viewing the map of entities deposited on said surface and producing an image of at least part of said map of entities.

8. The apparatus of claim 4 further comprising:
   at least one camera for viewing the map of physical entities deposited on said surface and producing an image of at least part of said map of entities;
   means for producing relative movement between said camera and said surface to scan the map of physical entities before said camera for viewing and imaging the physical entities; and
   a computer connected to said camera for controlling the operation of said camera, causing the camera to produce images of the physical entities at map positions on the surface, receiving said images and storing said images as a function of a map position.

9. An apparatus for monitoring and mapping entities comprising:
   a surface adapted to receive a deposit of entities;
   means for producing a stream of the entities;
   a sensor disposed in the stream of entities for measuring characteristics of the entities and producing an output indicative of the characteristics;
   means for presenting the stream of entities onto said surface for deposit;
   means for producing relative movement between said presenting means and said surface to deposit said entities on said surface;
   a computer having a clock for keeping time, being connected to said movement producing means, controlling the relative movement of said presenting means and said surface to produce a map of said entities on said surface in a desired pattern having a plurality of discrete map positions, determining the time at which the entities are deposited at each map position, storing the map positions as a function of time of entity deposit, said computer being connected to said sensor for receiving data as a function of time, and correlating the sensor data and the stored map positions by comparing the times stored in association with each of said map positions and said sensor data;
   at least one camera for viewing the map of entities deposited on said surface and producing an image of at least part of said map of entities;
   means for producing relative movement between said camera and said filter to scan the map of entities before said camera for viewing and imaging the entities; and
   said computer being connected to said camera for controlling the operation of said camera, causing the camera to produce images of entities at map positions on the surface, receiving said images and storing said images as a function of map position.

10. The apparatus of claim 9 further comprising said computer correlating the sensor data with the stored images by comparing the map positions associated with each of said stored images and said sensor data.

11. A map maker for operating on and topologically mapping physical entities comprising:
   a measuring station;
   first means for moving and presenting said physical entities in a first presentation to the measuring station;

a sensor for sensing a characteristic of said physical entities as they are presented and producing a sensor output corresponding to the characteristic;

second means for moving the physical entities from the measuring station to another location and for presenting said physical entities in a second presentation, different from said first presentation, to produce a map of physical entities; and computer means for correlating the sensor output with the map of physical entities.

12. A map for operating on and topologically mapping carded entities comprising:

a measuring station;

a carding machine for presenting uncarded entities in a first presentation to the measuring station, carding the entities as they leave the measuring station, and for presenting the carded entities in a second presentation to produce a map of carded entities;

a sensor for sensing a characteristic of the uncarded entities as the carding matching presents them to the measuring station; and computer means for correlating the sensor output with the map of carded entities.

13. A map maker for operating on and topologically mapping entities comprising:

a measuring station;

first means for presenting said entities in a first presentation to the measuring station;

a video camera for producing video images of said entities in said first presentation;

second means for transporting the entities from the measuring station to another location and for presenting said entities in a second presentation, different from said first presentation, to produce a map of entities; and computer means for correlating the sensor output with the map of entities.

14. The map maker of claim 13 further comprising:

a second video camera for producing video images of said entities in said second presentation; and said computer means being provided with a time delay correction factor corresponding to the time delay between when the entities are presented to the first camera and when the same entities are presented to the second camera, and correlating the video images of the first camera with the video images of the second camera based on the time at which the images were produced and the time delay correction factor.

15. A map maker for operating on and topologically mapping entities comprising:

a measuring station;

first means for presenting said entities in a first presentation to the measuring station;

a sensor for sensing a characteristic of said entities as they are presented and producing a sensor output corresponding to the characteristic;

second means for transporting the entities from the measuring station to another location and for presenting said entities in a second presentation, different from said first presentation, to produce a map of entities;

a video camera for producing video images of said entities in said second presentation; and computer means for correlating the sensor output with the map of entities, said computer means being provided with a time delay correction factor corresponding to the time when the entities are presented to said sensor and when the same entities are presented to the camera, and correlating the sensor output with the video images based on the time delay correction factor.

* * * * *